US00PP28778P2

(12) United States Plant Patent
Hansen

(10) Patent No.: US PP28,778 P2
(45) Date of Patent: Dec. 19, 2017

(54) ***LAGERSTROEMIA* PLANT NAMED 'LIKE A LATTE'**

(50) Latin Name: *Lagerstroemia indica*
Varietal Denomination: Like a Latte

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 25 days.

(21) Appl. No.: 14/999,716

(22) Filed: Jun. 17, 2016

(51) Int. Cl.
*A01H 5/00* (2006.01)

(52) U.S. Cl.
USPC ..... Plt./252

(58) Field of Classification Search
USPC ..... Plt./226, 252
See application file for complete search history.

*Primary Examiner* — Susan McCormick Ewoldt
*Assistant Examiner* — Karen Redden

(57) ABSTRACT

The new and distinct crape myrtle plant named *Lagerstroemia* 'Like a Latte' has a short broad-rounded habit, is ground hardy to at least USDA zone 6, has glossy reddish mahogany foliage that develops to a dark olive green color. The flowers are fragrant, large, self-cleaning white colored on current season growth.

2 Drawing Sheets

Botanical classification: *Lagerstroemia indica.*
Varietal denomination: 'Like a Latte'.

BACKGROUND OF THE INVENTION

The present invention relates to a new and distinct cultivar of the ornamental flowering shrub *Lagerstroemia indica* commonly known as crape myrtle, and hereafter referred to by the cultivar name 'Like a Latte'.

*Lagerstroemia* 'Like a Latte' originated from open-pollinated seed of *Lagerstroemia* 'White Chocolate' (not patented) collected by the inventor in the fall of 2010 at a cultivated area in Raleigh, N.C., USA. The resulting seedlings were grown in a full-sun, loamy-sand trial garden with water as needed and plants subjected to rigorous evaluations at a whole perennial nursery with goals for this program to produce improved, garden-worthy plants for the ornamental plant market of quality flower color and improved habit that would withstand cold temperatures. The single new plant meeting these criteria was originally assigned breeder code H10-07-01.

No plants of *Lagerstroemia* 'Like a Latte' have been sold, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

*Lagerstroemia* 'Like a Latte' was first asexually propagated from a single select plant in 2012 by stem cuttings at a wholesale perennial nursery in Zeeland, Mich. The resultant asexually propagated plants have been found to be stable and true to type in successive generations of asexual reproduction.

SUMMARY OF THE INVENTION

Plants of the new crape myrtle cultivar *Lagerstroemia* 'Like a Latte' have not been observed under all possible environmental conditions. The phenotype may vary somewhat with variations in environment such as light-intensity, temperature light-intensity, available moisture and fertility without, however, any variance in genotype.

The following traits in combination have been consistently observed and are determined to make up some of the unique characteristics of 'Like a Latte':

1. Short broad-rounded habit;
2. Ground (root) hardy to at least USDA zone 6;
3. Glossy foliage emerges reddish mahogany and develops to a dark olive coloring;
4. Large, fragrant, self-cleaning, white flowers on current season growth.

The nearest comparison crape myrtle varieties known to the inventor are: 'Gamad III' U.S. Plant Pat. No. 17,171, 'PIILAG-I' U.S. Plant Pat. No. 23,168, 'PIILAG-IV' U.S. Plant Pat. No. 23,478 and 'PIILAG B1' U.S. Plant Pat. No. 25,537 and the female parent 'White Chocolate'. All of the above comparison plants have flowers that start off as white, or nearly white. Compared to 'Gamad III' the new plant is slightly shorter and broader in habit. Compared to 'PIILAG-I' the new plant is shorter and more narrow in habit. Compared to 'PIILAG-IV' the new plant is significantly shorter and slightly narrower in habit. Compared to 'PIILAG B1' the new plant is slightly shorter in height and slightly broader in habit.

Compared to the female parent, 'White Chocolate', the new plant is significantly shorter in height and narrower in width of plant habit.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
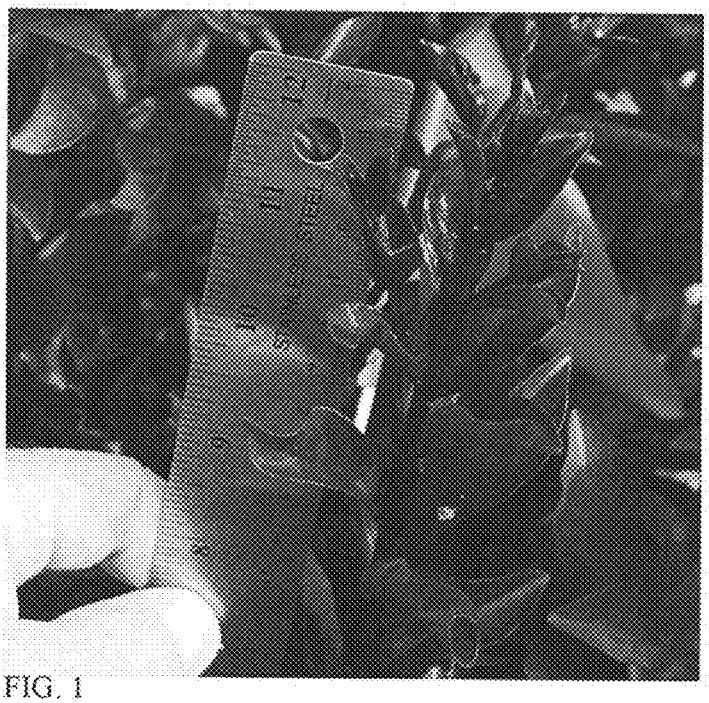
FIG. 1 shows a close-up of the young expanding foliage.
Figure 2:
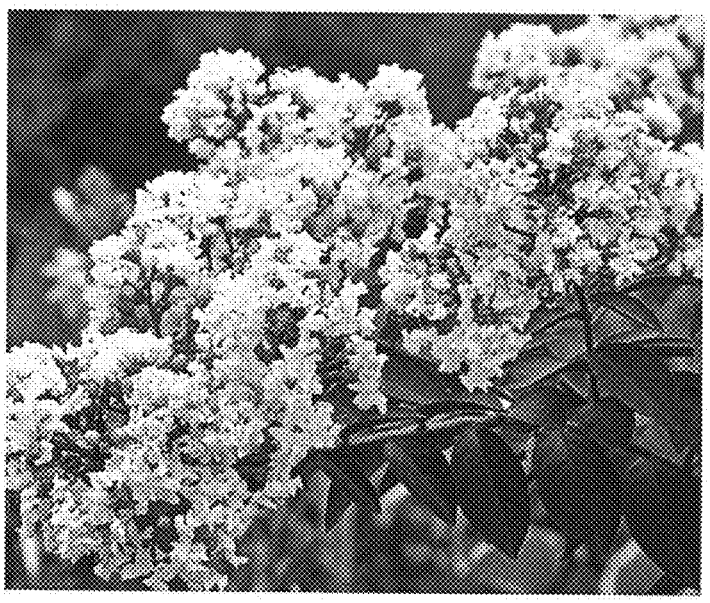
FIG. 2 shows a close-up of the flowers.
Figure 3:
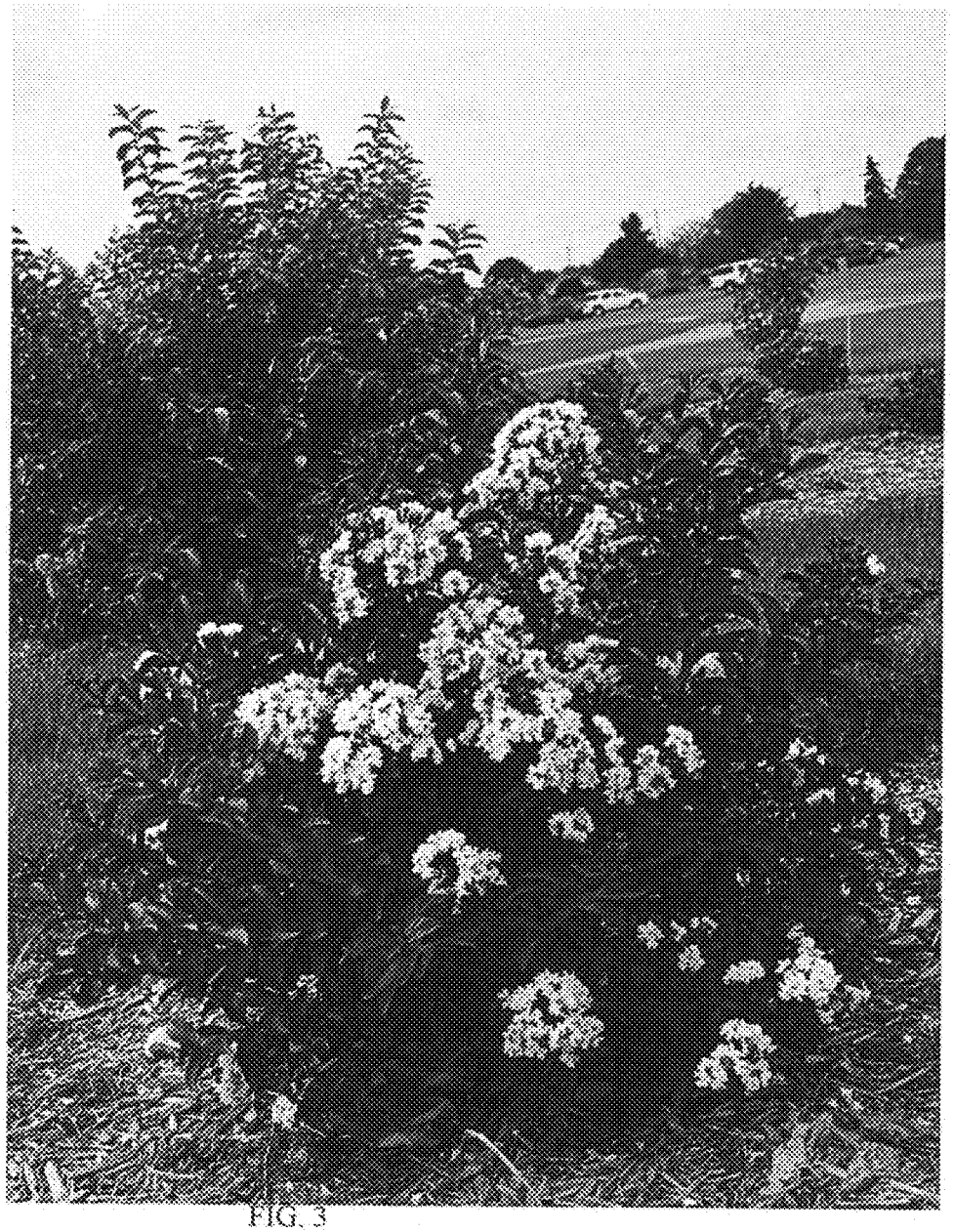
FIG. 3 shows the habit of a three-year-old plant in mid-season flowering.

The following botanical descriptions and color references are based on the 2001 edition of The Royal Horticultural Society Colour Chart except where common dictionary terms are used. Descriptions are based on two-year-old plants growing in a full-sun, trial garden with supplemental fertilizer and water as needed.

Plant description:

Habit: Mounded with extensive branching.

Plant size: Average about 40.0 cm tall and about 70.0 cm across about 20.0 cm above soil line.

Stems: Three main stems per plant; terete at base, average about 8.0 mm diameter at base; young stems slightly puberulent, with four longitudinal carina giving appearance of squaring, about 3.0 mm diameter toward apex; older basal stem exfoliating; attitude outward to upright.

Stem color: Young stems and carina with intense light nearest RHS N186C, shaded and undersides of young stems nearest RHS 145A; basal older woody stems nearest RHS 199B and broad longitudinal exfoliating striations of nearest RHS N199B.

Branches: Average 10 per main stem; to about 33.0 cm long; attitude upright to outward.

Nodes: About 28 nodes per main stem, average internode length about 10.0 mm.

Node color: Same as surrounding stem.

Leaves: Sub-opposite; elliptical; apex acute; base cuneate; margin entire ciliate; adaxial surface slightly laevigate and sparsely puberulent, abaxial laevigate and puberulent; average 4.7 cm long and 2.5 cm wide.

Young leaf color: Adaxial nearest RHS N186C with greenish undertones as ages of nearest RHS 138A; abaxial nearest N186C.

Mature leaf color: Adaxial nearest RHS 139A; abaxial nearest RHS 146A; ciliate margin nearest RHS 187C adaxial and abaxial.

Veins: Pinnate; micro-puberulent adaxial and sparsely abaxial.

Adaxial vein color: Young adaxial midrib blend between RHS 146A and RHS N186C, lateral veins nearest RHS N186C; young abaxial midrib between RHS 191A with tinting of nearest RHS N186C, and lateral veins nearest RHS N186C; mature leaf midrib nearest RHS 145C with lateral veins nearest RHS 146D.

Petiole: Puberulent abaxial and adaxial; adaxial slightly applanate; about 2.0 mm long and about 2.0 mm wide.

Petiole color: Adaxial and abaxial nearest RHS N186C on young expanding leaves; adaxial and abaxial between RHS N186C and RHS 183A.

Inflorescence: Panicle; average about 38 flowers; terminal panicles up to 100 flowers; up to about 12.0 cm long and about 15.0 cm across; beginning late-summer and continuing until fall, for about eight weeks.

Buds: Globose to ellipsoid; laevigate; glabrous; about 8.0 mm tall and 7.0 mm diameter one day prior to opening.

Bud color: Nearest RHS 143C at basal one-third, nearest RHS 187C distally with nearest RHS N186C between base and distil colors.

Flowers: Perfect; regular; actinomorphic; individually about 2.6 cm across and about 1.6 cm tall; lasting about two days.

Flower fragrance: Sweet, light.

Peduncle: Terete, with four longitudinal carinae; about 3.5 mm diameter at base, about 12.0 cm long.

Peduncle color: Nearest RHS N186C.

Pedicel: Terete; 4.0 mm to 8.0 mm long; average about 6.0 mm long and 1.0 mm diameter.

Pedicel color: Adaxial and abaxial blade white, lighter than RHS 155D.

Sepals: Fused in the basal 3.5 mm; apiculate apex, entire margin; glabrous and laevigate both adaxial and abaxial; about 7.3 mm long and individually about 3.8 mm long above the fusion and about 3.2 mm wide at fusion point.

Sepal color: Adaxial base lighter than RHS 142D, distally nearest RHS181D; abaxial base nearest RHS 138B, distally nearest RHS 187C.

Petals: Six; stalked; glabrous; blade ruffled or crisped; margin crisped; blade with rounded apex and cordate to sagittate base, to about 12.0 mm across and 10.0 mm long; claw base adnate to sepal; claw about 5.0 mm long and 0.5 mm diameter; overall about 1.5 cm long.

Petal color: Blade adaxial and abaxial white, lighter than RHS 155D when first opening and before dehiscing; claw nearest RHS 184C.

Androecium:

*Stamens*.—Total about 42; typically six longer and about 36 shorter.

*Filaments*.—Longer stamens to about 15.0 mm long and about 0.5 mm diameter, curled about 180 degrees in last 5.0 mm; shorter filaments nearly straight, about 9.0 mm long and less than 0.3 mm diameter; color of longer filaments base nearest RHS 61C and distally nearest RHS 158B, color shorter filaments nearest RHS 158D toward apex and nearest RHS N155B toward base.

*Anthers*.—Oblong; more developed on longer stamens to about 1.5 mm long and 1.0 mm across, on shorter stamens about 1.0 mm long and about 0.5 mm across; color nearest RHS 186B.

*Pollen*.—Abundant; color nearest RHS 10C.

Gynoecium: One.

*Style*.—Terete; glabrous; about 12.0 mm long and 1.0 mm diameter; color base between RHS 150D and RHS 145C in the middle portion and distally nearest RHS 174B.

*Stigma*.—Globose; about 1.2 mm diameter; color nearest RHS 187A.

*Ovary*.—Superior; globose; about 2.0 mm tall and 2.0 mm diameter; color between RHS 150D and RHS 145C.

Fruit: Globose; six-valved dehiscent capsule; about 7.0 mm wide and 7.0 mm tall; apex rostrate; base rounded.

Fruit color: Between RHS 200B and RHS 200A.

Seed: Lunate; about 5.0 mm long and 2.0 mm across at widest point.

Seed color: Between RHS 165B and RHS 165C.

Disease resistance: *Lagerstroemia* 'Like a Latte' has shown resistance to powdery mildew and black leaf spot, *Erisphe* and *Cercospora* fungi, respectively. Other resistance beyond that typical for crape myrtle has not been observed. The new plant's root system is capable of withstanding cold temperatures typical of those found in USDA zone 6.

I claim:

1. A new and distinct cultivar of crape myrtle plant named *Lagerstroemia* 'Like a Latte' essentially as herein illustrated and described.

* * * * *